United States Patent
Kim et al.

(10) Patent No.: US 9,949,868 B2
(45) Date of Patent: Apr. 24, 2018

(54) MANDIBULAR ADVANCEMENT DEVICE

(71) Applicant: ProSomnus Sleep Technologies, Inc., Pleasanton, CA (US)

(72) Inventors: Sung Kim, Pleasanton, CA (US); David W. Kuhns, Pleasanton, CA (US); Leonard A. Liptak, Pleasanton, CA (US); Laura Sheppard, Pleasanton, CA (US)

(73) Assignee: PROSOMNUS SLEEP TECHNOLOGIES INC., Pleasanton, CA (US)

( * ) Notice: Subject to any disclaimer, the term of this patent is extended or adjusted under 35 U.S.C. 154(b) by 0 days.

(21) Appl. No.: 15/416,666

(22) Filed: Jan. 26, 2017

(65) Prior Publication Data

US 2017/0143537 A1 May 25, 2017

Related U.S. Application Data

(63) Continuation of application No. 14/809,208, filed on Jul. 25, 2015, now Pat. No. 9,820,882, which is a
(Continued)

(51) Int. Cl.
*A61F 5/56* (2006.01)
*A61C 7/36* (2006.01)
(Continued)

(52) U.S. Cl.
CPC .............. *A61F 5/566* (2013.01); *A61C 7/08* (2013.01); *A61C 7/36* (2013.01); *B23C 3/00* (2013.01); *B23C 2226/61* (2013.01)

(58) Field of Classification Search
CPC .. A61F 5/56; A61F 5/563; A61F 5/566; A61F 2005/563; A61C 7/08; A61C 7/36;
(Continued)

(56) References Cited

U.S. PATENT DOCUMENTS 4,671,766 A * 6/1987 Norton ...................... A61F 5/01
433/6
4,708,646 A 11/1987 Jasper
(Continued)

FOREIGN PATENT DOCUMENTS

DE 102004007008 A1 9/2005
GB 2494935 A 3/2013
(Continued)

OTHER PUBLICATIONS

Notice of Allowance issued in U.S. Appl. No. 14/809,208 dated Mar. 16, 2017.
(Continued)

*Primary Examiner* — Ophelia A Hawthorne
*Assistant Examiner* — Camtu Nguyen
(74) *Attorney, Agent, or Firm* — Techlaw LLP; Sam K. Tahmassebi

(57) ABSTRACT

Disclosed herein are mandibular advancement devices comprising an upper splint and a lower splint, where the upper splint comprises one or more upper fins, where each upper fin is located at a distance UD from back of the upper splint; the lower splints comprise one or more lower fins, where each lower fin is located at a distance LD from back of the lower splint; where the position of the upper and lower fins is unchangeable. Also disclosed are methods of reducing partial constriction of airway during sleep for a patient, the method comprising identifying a patient in need thereof; and administering to the patient the disclosed mandibular advancement device. Also disclosed are methods of manufacturing a mandibular advancement device, the method comprising obtaining measurements from a patient's dentition; digitally designing a mandibular advancement device; and milling the mandibular advancement device.

12 Claims, 7 Drawing Sheets

Related U.S. Application Data continuation of application No. PCT/US2014/072398, filed on Dec. 24, 2014.

(60) Provisional application No. 61/922,016, filed on Dec. 30, 2013.

(51) Int. Cl.
*A61C 7/08* (2006.01)
*B23C 3/00* (2006.01)

(58) Field of Classification Search
CPC ..... A63B 71/05; A63B 71/085; B29C 69/001; B23C 2226/61
USPC .................................. 264/16, 138; 128/848
See application file for complete search history.

(56) References Cited

U.S. PATENT DOCUMENTS

| | | | |
|---|---|---|---|
| 5,313,960 A | 5/1994 | Tomasi | |
| 5,352,116 A | 10/1994 | West | |
| 5,365,945 A | 11/1994 | Halstrom | |
| 5,427,117 A | 6/1995 | Thornton | |
| 5,566,683 A | 10/1996 | Thornton | |
| 5,868,138 A | 2/1999 | Halstrom | |
| 6,041,784 A | 3/2000 | Halstrom | |
| 6,055,986 A | 5/2000 | Meade | |
| 6,161,542 A | 12/2000 | Halstrom | |
| 6,413,082 B2 | 7/2002 | Binder | |
| 6,418,933 B1 | 7/2002 | Strong | |
| 6,516,805 B1 | 2/2003 | Thornton | |
| 6,526,982 B1 | 3/2003 | Strong | |
| 6,604,527 B1* | 8/2003 | Palmisano | A61C 7/08 128/848 |
| 6,729,335 B1 | 5/2004 | Halstrom | |
| 7,146,982 B2 | 12/2006 | Mousselon | |
| 7,637,262 B2 | 12/2009 | Bailey | |
| D639,440 S | 6/2011 | Raad | |
| 8,001,973 B2 | 8/2011 | Sotos et al. | |
| 8,025,063 B2 | 9/2011 | Sotos et al. | |
| 8,037,886 B2 | 10/2011 | Sotos et al. | |
| 8,136,529 B2 | 3/2012 | Kelly | |
| 8,205,617 B2 | 6/2012 | Scarberry et al. | |
| 8,215,312 B2 | 7/2012 | Garabadian et al. | |
| 8,226,569 B2 | 7/2012 | Sotos et al. | |
| 8,267,093 B2 | 9/2012 | Marie-Catherine | |
| 8,312,884 B2 | 11/2012 | Fuselier | |
| 2007/0183572 A1* | 8/2007 | Drummond | A61F 5/566 378/98.8 |
| 2007/0283967 A1* | 12/2007 | Bailey | A61F 5/566 128/848 |
| 2010/0316973 A1* | 12/2010 | Remmers | A61F 5/566 433/214 |
| 2011/0005527 A1 | 1/2011 | Andrew et al. | |
| 2011/0308531 A1 | 12/2011 | Grosky | |
| 2013/0014765 A1 | 1/2013 | Meade | |

FOREIGN PATENT DOCUMENTS

| | | |
|---|---|---|
| KR | 20130111848 A | 10/2013 |
| WO | 2009140720 A1 | 11/2009 |
| WO | 2013102095 A1 | 7/2013 |
| WO | 2013124452 A1 | 8/2013 |

OTHER PUBLICATIONS

Partial European Search Report and Provisional Opinion issued in EP 14877266 dated Jul. 24, 2017.
Bloch et al., A Randomized, Controlled Crossover Trial of Two Oral Appliances for Sleep Apnea Treatment. Am J Respir Crit Care Med. Jul. 2000;162(1):246-251.
Demko, Course 3106: Obstructive Sleep Apnea: A Whirlwind Tour. Lecture Slides, Oregon Dental Conference. Apr. 4, 2013:39 pages.
Fritsch et al., Side Effects of Mandibular Advancement Devices for Sleep Apnea Treatment. Am J Respir Crit Care Med. Sep. 1, 2001;164(5):813-818.
Lin and Lee, Patents Analysis and Design Suggestions for the Mandibular Advancement Devices. Taiwan International Journal of Medical and Biological Sciences, 2012;6:103-108.
Lowe, "Dental Appliances for the Treatment of Snoring and Obstructive Sleep Apnea;" Ch. 69 in Principles and Practice of Sleep Medicine, 2nd Ed.; edited by Kryger, MH, et al.; 1994; W.B. Saunders Company, Philadel. :722-735.
Mehta et al., A Randomized Controlled Study of a Mandibular Advancement Splint for Obstructive Sleep Apnea. Am J Respir Crit Care Med. May 2001;163(6):1457-1461.
Nordstrom, The NorSnor-2 Product Pages. Murdock Laboratory Jun. 1994:1-3.
O'Sullivan et al., Mandibular advancement splint: an appliance to treat snoring and obstructive sleep apnea. Am J Respir Crit Care Med. Jan. 1995;151(1):194-198.
Tan et al., Mandibular advancement splints and continuous positive airway pressure in patients with obstructive sleep apnoea; a randomized cross-over trial. Eur J Orthod. Jun. 2002;24(3):239-249.
Wahl, Orthodontics in 3 millennia. Chapter 9: Functional appliances to midcentury. Am J Orthod Dentofacial Orthop. Jun. 2006;129(6):829-833.

\* cited by examiner

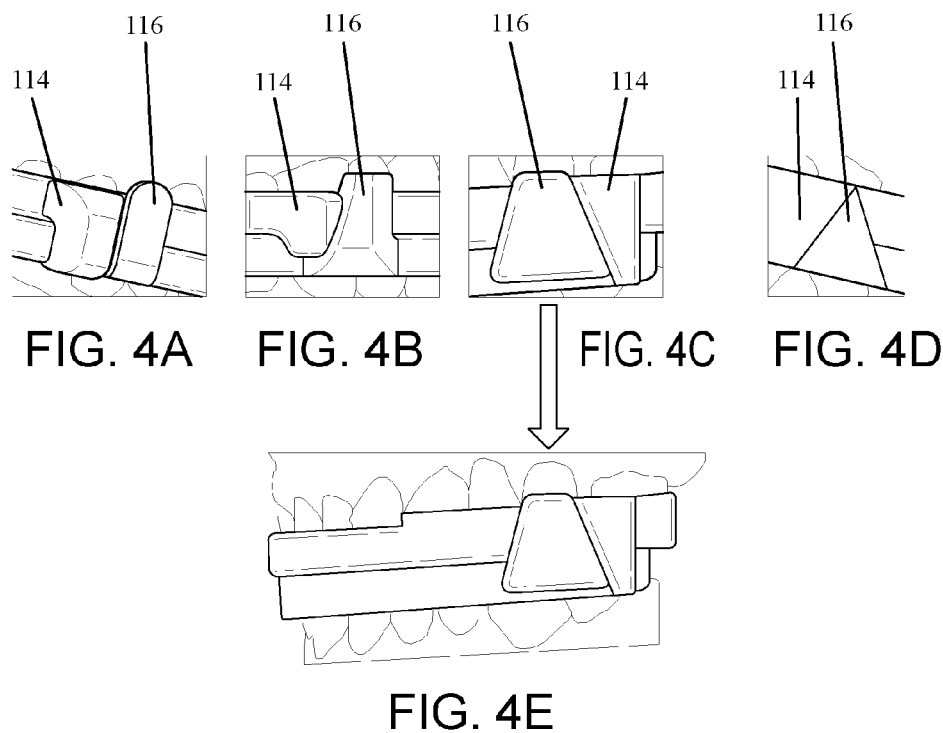
FIG. 4A  FIG. 4B  FIG. 4C  FIG. 4D
FIG. 4E
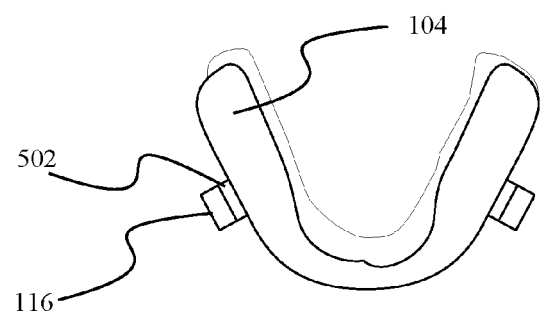
FIG. 5

MANDIBULAR ADVANCEMENT DEVICE

RELATED APPLICATIONS

This application is a continuation of the U.S. application Ser. No. 14/809,208, filed on Jul. 25, 2015, by LIPTAK et al., and entitled "MANDIBULAR ADVANCEMENT DEVICE," which in turn is a continuation of the International Application PCT/US2014/072398, filed Dec. 24, 2014, which designates the U.S. and claims priority to the U.S. Provisional Application Ser. No. 61/922,016, filed on Dec. 30, 2013, by David Kuhns et al., and entitled "MANDIBULAR ADVANCEMENT DEVICE," the entire disclosure of all the above applications is incorporated herein by reference, including all the drawings.

FIELD OF THE INVENTION

The present invention is in the field of medical devices, and in particular it is in the field of mandibular advancement devices.

BACKGROUND OF THE DISCLOSURE

Snoring and mild sleep apnea are generally thought to be the result of a reduced or partial constriction of the airway during sleep. This may be attributed to soft tissue sinking and applying pressure on the airway during sleep including the mandible dropping and moving backwards. Mandibular advancement devices are designed to move the mandible forward to relieve the force applied from soft tissue during sleep and assisting in opening the airway. Depending on the patient, the advancement of the mandible may vary based on the response of the patient. Optimizing the adjustment is referred to as titration.

Many devices are on the market today that serve to advance the mandible. A dual arch device comprising fins and an adjustment screw block are represented by Somnomed's Somnodent (U.S. Pat. No. 6,604,527), the Dynflex Dorsal Appliance, and Dr. Nordstrom's NorSnor II produced by Murdock Labs since the 1980's. Each device has an adjustable upper screw mechanism with block, which upon adjustment applies a force against a lower fin or bite block that then moves the mandible forward. The threaded screw system, requires that the user apply an Allen wrench to adjust the screw for titration. These devices are handmade and built up using polymethylmethacrylate (PMMA) and the corresponding monomer, methylmethacrylate. The device is cured in the dental lab and custom designed for each patient. Reproduction of the quality and accuracy of the device is subject to human skill.

Alternatively, there are devices that make an adjustment by changing out straps of different lengths to titrate the mandible forward. Examples of these are the Silent Nite (U.S. Pat. No. 5,365,945) produced by Glidewell, and the Narval (U.S. Pat. No. 7,146,982) produced by Resmed. These devices offer a possibly lower profile than the screw adjustment devices and also connect the upper and lower arch together.

Several limitations exist with these existing sleep apnea devices. First, the manual, artisanal fabrication method used by these devices limits the ability to consistently and precisely transfer the prescription into the device design. This limitation results in the need for additional adjustments. Second, the manual artisanal fabrication method requires the layering of monomers, which can subject the patient to higher levels of residual monomers. Third, existing device designs feature multiple components, straps, and screws that decrease durability, reliability, and ease of use. Fourth, the materials used in the manual, artisanal fabrication method require the device to be of a certain size to effectively withstand the normal intraoral forces that the device is subjected to. This size limitation results in decreased patient comfort and patient compliance.

Therefore a need exists to provide a mandibular advancement device that provides advancement of the lower jaw through a series of splints digitally designed and milled to provide accurate increments of advancement for easy titration of the mandible, without the need for an adjustment screw mechanism or adjustment straps.

SUMMARY OF THE INVENTION

Disclosed herein are mandibular advancement devices comprising an upper splint and a lower splint, where the upper splint comprises one or more upper fins, where each upper fin is located at a distance UD from back of the upper splint; the lower splints comprise one or more lower fins, where each lower fin is located at a distance LD from back of the lower splint; where the position of the upper and lower fins is unchangeable. Also disclosed are methods of reducing partial constriction of airway during sleep for a patient, the method comprising identifying a patient in need thereof; and administering to the patient the disclosed mandibular advancement device. Also disclosed are methods of manufacturing a mandibular advancement device, the method comprising obtaining measurements from a patient's dentition; digitally designing a mandibular advancement device; and milling the mandibular advancement device. Also disclosed are methods of selecting a mandibular advancement device for a patient, the method comprising a) obtaining two or more upper splints of the mandibular advancement device, wherein each upper splint comprises one or more upper fins, wherein each upper fin is located at a distance UD from back of the upper splint, and wherein the distance UD of any of the two or more upper splints is different than the distance UD of any other of the two or more upper splints; and obtaining two or more lower splints of the mandibular advancement device, wherein each lower splint comprises one or more lower fins, wherein each lower fin is located at a distance LD from back of the lower splint, and wherein the distance LD of any of the two or more lower splints is different than the distance LD of any other of the two or more lower splints; b) choosing a combination of one upper splint and one lower splint for the patient; c) observing the clinical outcome of the chosen combination of one upper splint and one lower splint; d) choosing a different combination of one upper splint and one lower splint for the patient if the clinical outcome of step c) is unacceptable; and e) repeating steps b)-d) until an acceptable clinical outcome is obtained.

BRIEF DESCRIPTION OF THE DRAWINGS

FIG. 1A illustrates a front view of an embodiment of the disclosed mandibular advancement device as it is worn in the mouth, whereas

FIG. 4A illustrates an embodiment of the fin design in a predesigned digital library of fins. FIG. 4B illustrates another embodiment of the fin design in a predesigned digital library of fins. FIG. 4C illustrates another embodiment of the fin design in a predesigned digital library of fins. FIG. 4D illustrates another embodiment of the fin design in a predesigned digital library of fins. FIG. 4E illustrates that a fin design from the library is incorporated into an embodiment of the disclosed mandibular advancement device.

FIG. 5 illustrates an embodiment of the disclosed mandibular advancement device where there exists a gap between the lower fin and the lower splint.

FIG. 8A shows a free standing upper splint with the retention arms, while

DETAILED DESCRIPTION OF THE EMBODIMENTS

Figure 1A:
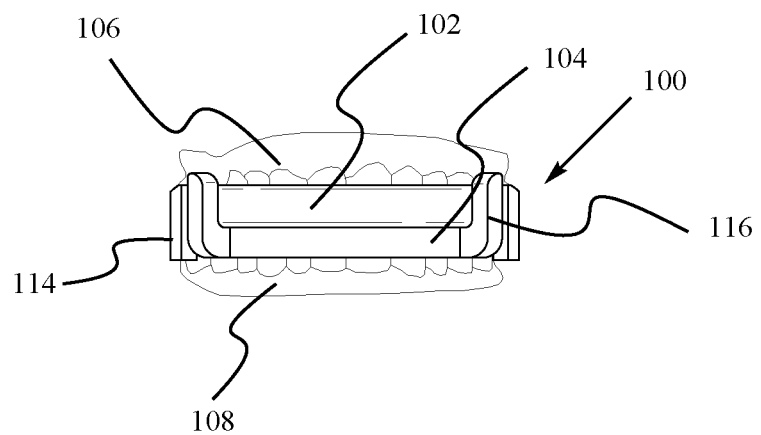

In one aspect provided herein is a digitally designed and milled mandibular advancement device comprising an upper splint and a lower splint, wherein the upper and lower splints independently further comprise one or more fins. In some embodiments, the splints provide accurate increments of advancement of the lower jaw for titration of the mandible. The terms "dental splint" and "splint" as used herein refers to several types of orthodontic devices that are designed to address dental problems such as loose teeth and bruxism, in addition to problems with snoring and apnea.

A patient in need of the disclosed mandibular advancement devices wears the upper splint on the upper dentition and the lower splint on the lower dentition during sleep. The splints are designed to remain attached to the dentition until the patient removes them. The fins of the upper and lower splints cause a precise placement of the mandible in relation to the maxilla. The mandible is caused to stay in a forward position and does not relax and fall back. The airway constriction during the sleep is thereby minimized.

In one embodiment the device creates an offset between the upper and lower splint by using upper and lower fins as boundary surfaces to restrict movement while the mouth is closed or reasonably opened.

In some embodiments, the devices disclosed herein were digitally designed and then milled as a single unit. In some of these embodiments, a computer aided design (CAD) process were used to design and manufacture the mandibular advancement devices disclosed herein. A plaster model of the patient's dental impression were first obtained using well-known techniques in the art. Then, scans of the plaster models were imported into the CAD software. In other embodiments, the 3D files of the patient's impression are imported from other sources, such as a direct scan of the patient dentition using an Intra Oral Scan (IOS) Device, e.g., the 3M TruDef™ scanner, or a direct scan of the impression from either an IOS or Cone Beam Computed Tomography (CBCT) device. In these embodiments, the files enable the design of the mandibular advancement splint in 3D space in a CAD software such as 3-Matic by Materialise™.

In other embodiments, the different components of the disclosed devices, for example the splint, the fins, the retention arms, etc., are milled or manufactured separately and then attached together after the manufacturing. This approach allows for the use of interchangeable parts.

In one embodiment the digitally designed and milled splints are reproduced accurately without manual polymer buildup. In some embodiments, accurate reproduction results in accurate replacement devices. In other embodiments, it results in reproducible titration settings. In some embodiments the splints are digitally designed and milled to provide access to pre-cured polymeric materials, and wherein the device has minimal residual monomers.

In one embodiment one or more identifying information, e.g., the patient's name, order number, and other relevant tracking information, are designed into the device. The identifying information appears on the device through the milling process.

In one embodiment, the device is designed to comfortably fit on to a patient's upper and lower arches, maintain a maximum amount of space for the tongue, and keep the mandible advanced forward per a doctor's prescription while still allowing the patient to reasonably open their mouth and move their jaw from left to right for comfort. This contact serves as a barrier to keep the lower fin in a position forward of this fin engagement surface.

The disclosed devices can be made from any material that can withstand the oral environment for an extended period of time, for example overnight. Furthermore, the material can be any material that is capable of being milled to form the devices disclosed herein. Examples of materials include plastics and other polymers, whether hard or soft, transparent or opaque. Some suitable polymers include, but are not limited to, a polyetheretherketone (PEEK), polystyrene, polyvinyl chloride, rubber, synthetic rubber, or an acrylate polymer, such as a polymer made up of methyl methacrylate, methyl acrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA).

Embodiments of the device are further described with reference to the accompanying drawings.

Figure 1B:
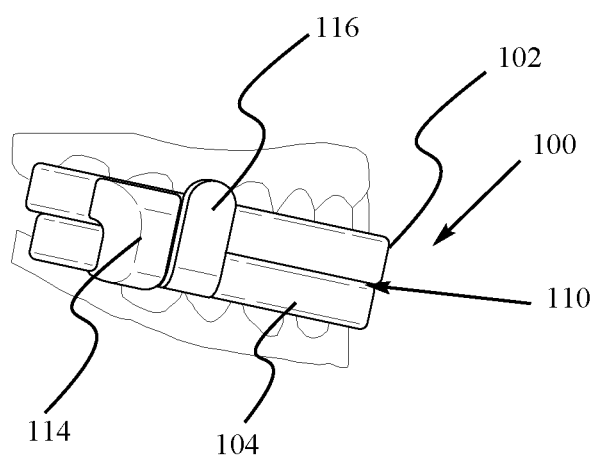
FIG. 1B shows a side view of the same embodiment.

FIG. 1 illustrates an embodiment of the disclosed mandibular advancement device, 100. FIG. 1a shows a front view of the device as it is worn in the mouth, whereas FIG. 1b shows a side view of the same embodiment. The device 100 comprises and upper splint 102 and a lower splint 104. The splint 102 is configured to fit snuggly onto the upper dentition 106, while the lower splint 104 is configured to fit snuggly onto the lower dentition 108. Each splint provides enough retention to keep the device on during normal wear but allowing the user to pull off the device with minimal effort. The two splints contact each other along the occlusal plane 110, i.e., the plane passing through the biting surfaces of the teeth.

In one embodiment the thickness of the upper splint 102 and lower splint 104 is independently varied to create a fixed amount of jaw opening between the patient's arches.

The devices 100 disclosed herein are prepared individually and specially for a particular patient. For this reason, while preparing the digital design of the disclosed devices, the idiosyncrasies of the patient's oral and dentition structures are taken into account. For instance, in some embodiments, the opposing surfaces of the splint are designed in variance with each other to accommodate the patient's oral structure to achieve maximum comfort. The surfaces can be flat, or be made to touch at one or more points. This is true of any other feature of the devices 100. For example, the height, width and shape of the fins; the rake angle; the offset position of the fins; the location of retention arms, if any; the dental impressions; inter alia, are designed specifically for the particular patient. This feature is easily enabled with a device that is digitally pre-designed. The currently available devices are handmade, making it difficult for the artisan to accurately take into account the specific oral features of a particular patient.

Each upper splint 102 comprises at least one upper fin 114, and preferably two upper fins 114. The fin 114 is located to the side of the upper splint 102 such that when the splint 102 is worn by the patient, the fin 114 is near the molars. Each upper fin 114 protrudes downwardly.

Similarly, each lower splint 104 comprises at least one lower fin 116, and preferably two lower fins 116. The fin 116 is located to the side of the lower splint 104 such that when the splint 104 is worn by the patient, the fin 116 is near the molars. Each lower fin 116 protrudes upwardly.

Throughout the present disclosure, the terms "up," "upper," or "upward," and "down," "lower," or "downward" refer to the relative position of the upper jaw and the lower jaw. Thus, "protruding downwardly" means protruding away from the upper jaw and towards the lower jaw. Similarly, the words "front" or "forward" and "back" or "backward" refer to the relative position of components in the mouth. Thus, "front" means towards the lips, whereas "back" means towards the throat, when the device is in the mouth.

Figure 2A:
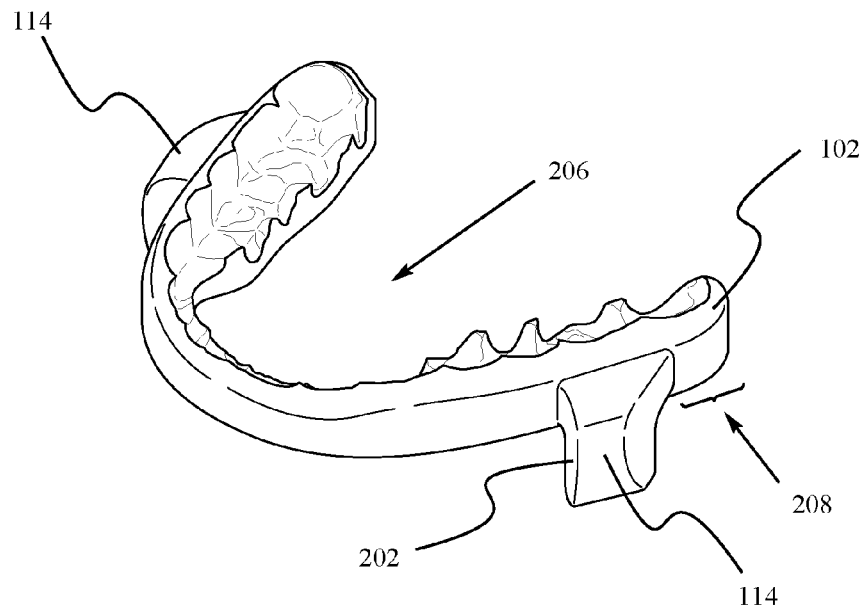
FIG. 2A illustrates an embodiment of the upper splint of the disclosed mandibular advancement devices where the rake angle is set in a neutral orientation.
Figure 2B:
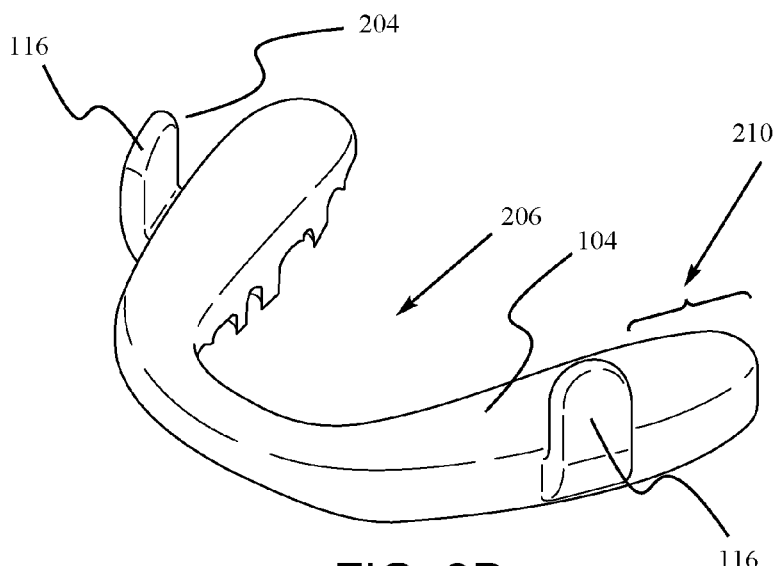
FIG. 2B is an illustration of an embodiment of the lower splint.

FIG. 2A shows the embodiment of the upper splint that is shown in FIG. 1 and FIG. 2B shows the embodiment of the lower splint that is shown in FIG. 1. FIG. 2 depicts the splints by themselves and without being worn on the teeth.

The upper fin 114 comprises a front surface 202 and the lower fin 116 comprises a back surface 204. When the device is worn in the mouth, the lower fin 116 is located in front of the upper fin 114. The front surface 202 of the upper fin 114 contacts the back surface 204 of the lower fin 116. This contact serves as a barrier to keep the lower fin in a position forward of this fin engagement surface. That is, the contact prevents the lower fin from moving backward relative to the upper jaw. Thus, once the device is worn, the relative forward position of the upper and lower jaws becomes fixed. The patient would be able to open and close their mouth and move the lower jaw from left to right for comfort. However, the patient would not be able to move the lower jaw backwards beyond the point of contact of the two surfaces 202,204.

In one embodiment the device is digitally designed and milled to provide optimal strength with reduced interference to the tongue creating a comfortable and durable device. As seen in FIGS. 2A & 2B, the two splints each form an arch with an empty center 206. The empty center 206 provides room for the patient's tongue when the device is in use. The type of design that allows room for the tongue is referred to as lingual-less. Thus, some embodiments of the present device 100 are lingual-less designs.

The upper fin 114 is located at a distance UD (208) from the back of the upper splint 102. Similarly, the lower fin 116 is located at a distance LD (210) from the back of the lower splint 104. Distances 208,210 are also referred to as fin offset. The relative positioning of the fins determines the degree to which the lower jaw is protruded forward, i.e., the jaw offset. As discussed below, in some embodiments, the distances 208 and 210 are manipulated to provide the best fit for the patient.

Figure 3A:
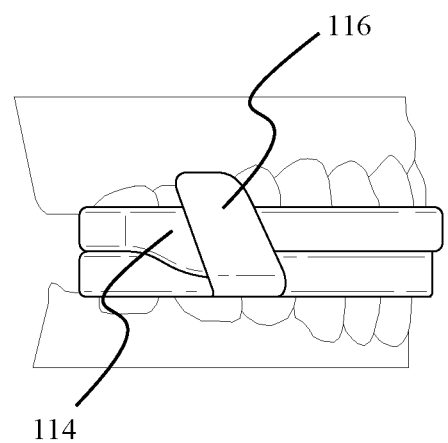
FIG. 3A illustrates an embodiment of the disclosed mandibular advancement device where the rake angle is set in a recline orientation.
Figure 3B:
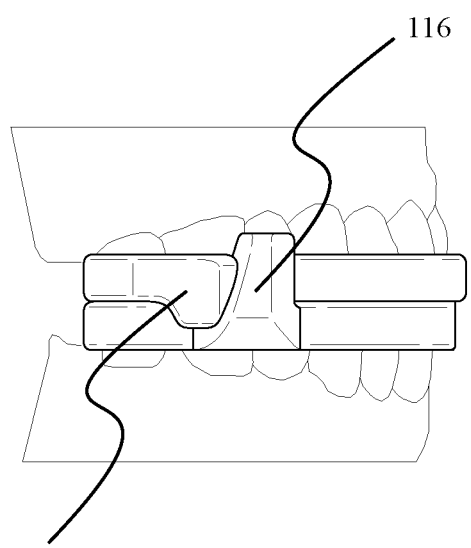
FIG. 3B illustrates an embodiment of the disclosed mandibular advancement device where the rake angle is set in a procline orientation.

In one embodiment, the upper and lower fins vary in angular shape at the contact surfaces of each fin to provide the most anatomically correct position and comfort during the motion of opening and closing the mouth. The embodiment shown in FIG. 1 comprises vertical contact surfaces. In these embodiments, the contact surfaces 202 and 204 are perpendicular to the occlusal plain 110. In this embodiment, the rake angle, i.e., the angle that surface 202 makes with the occlusal plane 110, is 90° to the occlusal plane, i.e., a neutral angle. In other embodiments, for example those shown in FIGS. 3A and 3B, the contact surfaces are at a non-neutral angle. For example, in the embodiment shown in FIG. 3A, the rake angle is set in a recline orientation. In this embodiment, the surface 202 angles backward. Conversely, in the embodiment shown in FIG. 3B, the rake angle is set in a procline orientation. In this embodiment, the surface 202 angles forward. The rake angle is configured to drive a directional movement during the opening and closing of the mouth. The particular angle, i.e., whether neutral, incline, or procline, and the angle degree, are chosen based on clinician prescription and patient comfort.

In one embodiment, the fins are selected from a predesigned digital library of fins. FIG. 4 shows additional embodiments of the fin design. FIGS. 4A-4D show some of the embodiments used in a fin library. In some embodiments, a designer calls from a library of fin designs, for example those shown in FIGS. 4A-4D, select one fin type (for example that shown in FIG. 4C), and place onto the custom patient splint design, as shown in FIG. 4E.

In some embodiments, for example that shown in FIG. 5, there exists a gap 502 between the lower fin 116 and the lower splint 104. While the fin 116 is attached to the splint 104 at the base, the fin 116 protrudes slightly outwards before protruding upward. In some embodiments, a corresponding gap exists between the upper fin 114 and the upper splint 102. The gap 502, if present, is designed into the device based on the prescription and patient anatomy and comfort. The gap 502 further allows for the side to side motion of the lower jaw with respect to the upper jaw.

Figure 6:
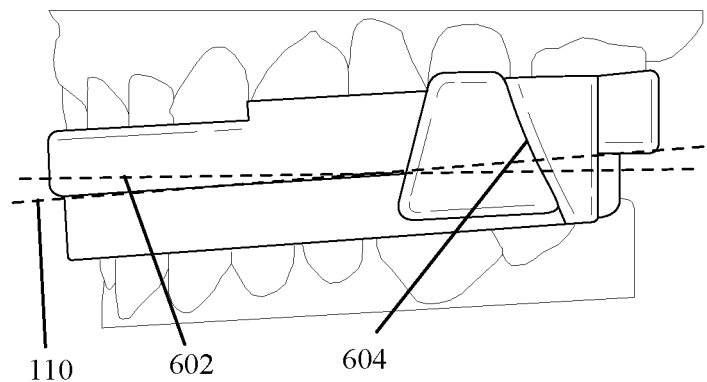
FIG. 6 illustrates varying the plane of the splint with respect to the occlusal plane.

When the device is worn by a patient and the patient's mouth is closed, the bottom surface of the upper splint and the top surface of the lower splint contact each other along the curve of the device, i.e., the arch of the mouth. The two surfaces contact each other along the plane of the splint. In one embodiment the opposing surfaces of the splint are designed such that the plane of the splint equals the occlusal plane. In some embodiments the plane of the splint is at an angle to the occlusal plane. FIG. 6 illustrates the ability to design devices in varying degrees of angle of the plane 110 of the splint to the occlusal plane 602. In CAD, the angle of the plane 110 of the splint can be adjusted within the sagittal plane relative to the patient's anatomical occlusal plane 602. Moreover the angle of the plane 110 can be adjusted within the frontal plane relative to the patient's occlusal plane 602.

Both adjustments are useful to the clinician to affect changes to the relative positioning of the mandible and maxillae. The path of the movement of the upper and lower arches, for the opening and closing of the mouth, is affected by the engagement surface 604, i.e., where the contact surfaces 202 and 204 meet. If the engagement surface 604 is not properly designed, then the upper and lower arches open and close along an unnatural arc, causing pain for the patient. In manufacturing the disclosed devices 100, the natural arc of the patient's jaw movement is taken into account in the digital design. The engagement surface 604 is then designed to fit the natural arc.

In some embodiments, the device 100 is made of transparent materials, for example transparent plastic, to allow the clinician to see the patient's dentition through the device 100 to ensure good fit. Thus, in some embodiments, the clinician can insert a generic device 100 into the patient's mouth and mark the various measurements on the transparent device 100 instead of preparing a dental impression. In other embodiments, a transparent device 100 is prepared first, and relatively inexpensively, and the fit is tested before a more expensive and permanent device is manufactured.

In some embodiments the fins vary in length. In certain embodiments, the fins are adjusted to the patient's open mouth dimensions. In some embodiments, the fins vary in length related to the opposing fin to optimize the length required to maintain mandible offset position while considering comfort such that each fin is the same length or a fraction of the length of the opposing fin. The sum of the heights of an upper fin 114 and lower fin 116 is the total range of contact along the engagement surface before the two splints are separated. At the point of separation, the two splints do not exert pressure on each other and do not provide any jaw offset. In some embodiments, the upper fin 114 and lower fin 116 are of equal heights. In these embodiments, the total range is optimized while minimizing the height of either fin. The ratio of the heights of each fin can also be adjusted for patient comfort or clinical reasons.

In some embodiments, the thickness of each fin can be adjusted to apply more or less pressure against the cheek. The pressure on the cheek stimulates the body to adjust the muscles in the mouth area, e.g., the airway muscles, for patient comfort or clinical reasons.

In one embodiment the device embeds one or more structural features that create strength using less material. In some embodiments the structural feature is made from a single material. The term "embed" as used herein refers to a single material with design geometries or purposefully milled slots or other geometries that enable another material to be added as a support member, in the same way a rebar can strengthen a concrete block. In some embodiments the structural feature is made from a combination of materials, such as a metal alloy. In some embodiments the metal or metal alloy is in the shape of a ball clasp, retention wire, or treatment wire. In some embodiments the treatment wires comprise of wires to aid in a clinical result deemed important by the practicing doctor, such as retention wires, alignment wires, or a tongue behavior modification wire such as spikes or barbs to affect tongue thrust.

A patient inserts the disclosed devices 100 into the patient's mouth before sleep and removes them after sleep. The devices should be retained in the mouth snugly enough so that the device does not fall out while the patient is sleeping. However, the fit cannot be too snug so that the patient cannot easily remove the device after waking up. The retention of the device 100 in the mouth is achieved using a combination of one or more of a variety of retention devices and gaps in space between the device and tissue.

Figure 7:
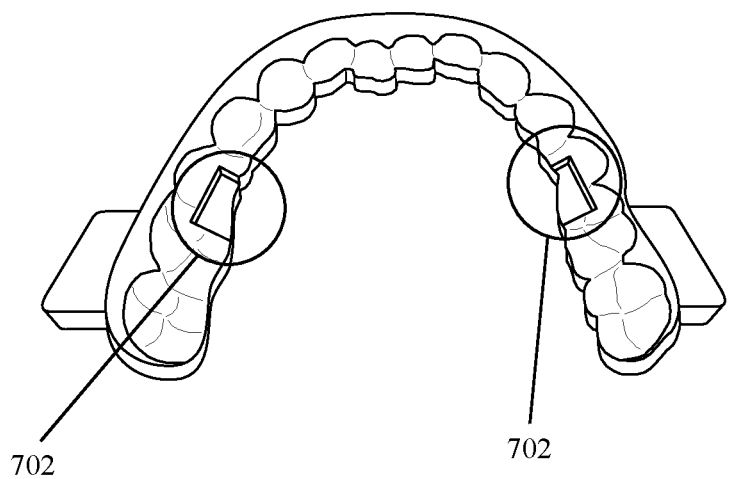
FIG. 7 shows the occlusal side of a splint with cutouts designed into the device to accurately place ball clasps.

In one embodiment the device is retained onto the teeth of a patient using patient specific retention arms. In some embodiments, the retention arms replace or improve the classic use of ball clasps. In the embodiments where ball clasps are used, space for their placement can easily be designed into the splint. In one embodiment, FIG. 7 shows the occlusal side of a splint with cutouts 702 designed into the device to accurately place ball clasps.

Figure 8A:
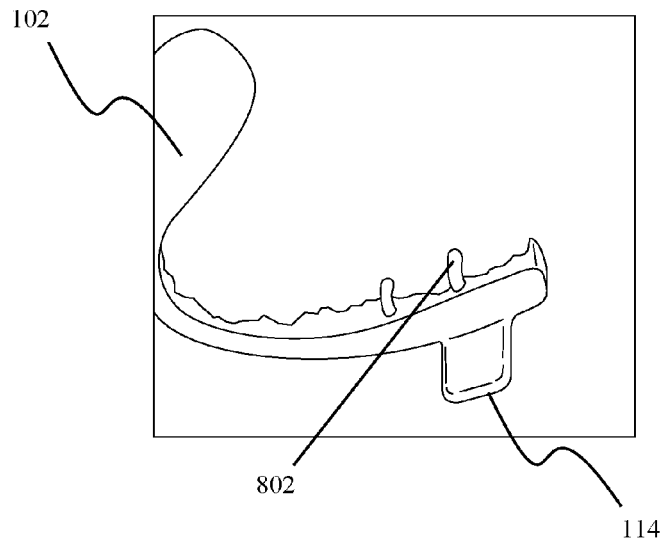
Figure 8B:
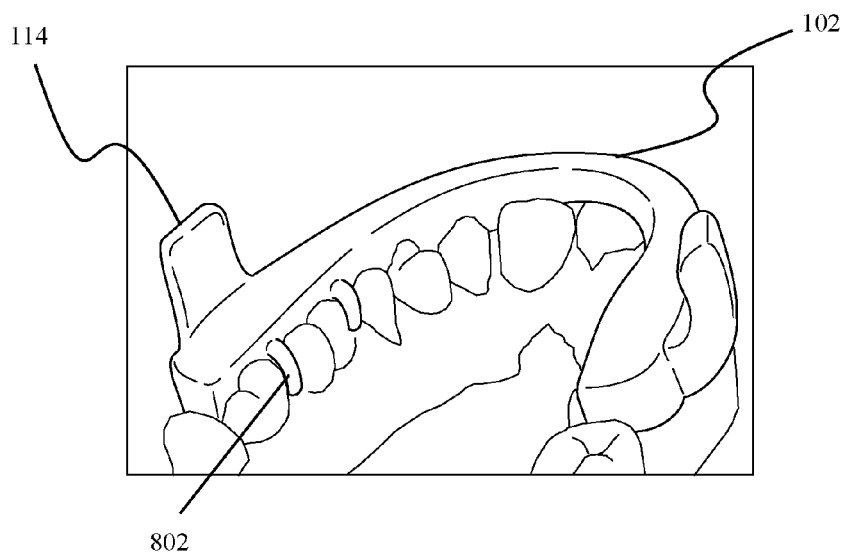
FIG. 8B shows the graphics of how the upper splint and the retention arms fit into the mouth of the patient.

In some embodiments, for example that shown in FIG. 8, the device 100 comprises retention arms 802, built into either or both of the upper splint 102 and lower splint 104. The retention arms 802 allow for a more secure placing of the splints into the mouth. FIG. 8A shows a free standing upper splint 102 with the retention arms 802, while FIG. 8B shows the graphics of how the upper splint 102 and the retention arms fit into the mouth of the patient. In some embodiments, the retention arms 802 take on the shape of the classic ball clasp, while in other embodiments, the retention arms 802 perfectly conform to the patient's anatomy to optimize strength and surface area for retention while allowing for maximum space for the tongue.

In some embodiments, a gap is designed between a particular device surface and one or more surfaces of a patient's anatomy. A purpose of the gaps is to allow the device 100 to be installed easily, stay retained under normal conditions, and be removed easily as well. In some embodiments, the gap is uniform across the entire contact region between the device and the patient's tissue. In other embodiments, the gap is strategically placed with properly designed spacing to provide easy installation of the device in the mouth, optimal device retention onto the patient's dentition, or ease of use of the device. The gap is easily programmed into the CAD digital design. Because the disclosed device can be prepared quickly and inexpensively, the clinician or the designer can experiment with a series of different gap placings until the best fit is obtained.

It is possible, through a series of steps, called titration, to choose the device having the most clinically relevant mandibular advancement setting for the patient. Thus, in another aspect, disclosed herein methods of selecting a mandibular advancement device for a patient, the method comprising:

a) obtaining two or more upper splints of the mandibular advancement device, wherein each upper splint comprises one or more upper fins, wherein each upper fin is located at a distance UD from back of the upper splint, and wherein the distance UD of any of the two or more upper splints is different than the distance UD of any other of the two or more upper splints; and obtaining two or more lower splints of the mandibular advancement device, wherein each lower splint comprises one or more lower fins, wherein each lower fin is located at a distance LD from back of the lower splint, and wherein the distance LD of any of the two or more lower splints is different than the distance LD of any other of the two or more lower splints;

b) choosing a combination of one upper splint and one lower splint for the patient;

c) observing the clinical outcome of the chosen combination of one upper splint and one lower splint;

d) choosing a different combination of one upper splint and one lower splint for the patient if the clinical outcome of step c) is unacceptable; and e) repeating steps b)-d) until an acceptable clinical outcome is obtained.

Once a digital scan of the patient's dentition is obtained, a number of upper and lower splints are milled for the patient. Each of the upper and lower splints has a different fin offset setting. The clinician chooses one set of upper and lower splints for the patient. If the patient's condition is not improved sufficiently, the clinician then chooses another set of splints. This process is continued until a set of splints providing the best clinical outcome is chosen. An advantage of the devices and methods disclosed herein is that by digitally designing the splints and automatedly manufacturing them, several splints can be prepared relatively quickly and inexpensively. Further, the digital design allows for a precise positioning of the fins. A more effective mandibular advancement can then be obtained than by using a hand-milled and hand-cranked device.

In some embodiments, the titration settings provide for a flexible positioning of the fins in the mouth in the mesial-distal direction. In some embodiments, the fit of the device 100 on a patient is titrated through the use of devices 100 with varying distances 208 and 210 (see FIG. 2). In certain embodiments, the device 100 is milled directly from a CAD file such that the accuracy of the data from the impression of the patient's anatomy, the fit of the device to that data, and the design of the device are precisely transferred to the milling machine. This enables very precise design adjustment in positioning each of the fins in the splint, i.e., the measurement of the distances 208 and 210, and in their position relative to each other in a reproducible and manufacturable way.

For example, in one embodiment, three different upper splints 102 were manufactured having increasingly longer distances 208, i.e., longer fin offset. Also, two different lower splints 104 were manufactured having two different distances 210. Thus, pairing one lower splint 104 with one upper splint 102 provided one jaw offset, while pairing the same upper splint 102 with a different lower splint 104 provided another jaw offset, and so on.

An illustrative example is shown in Table 1. To compile this table, five different upper splints 102 were prepared having 0.0 mm, 1.0 mm, 2.0 mm, 3.0 mm, and 4.0 mm fin offset (distance 208), respectively. Also, four different lower splints 104 were prepared having 0.0 mm, 0.5 mm, 1.0 mm, and 2.0 mm fin offset (distance 210), respectively. The combination of the two different splints can provide a jaw offset ranging from 0.0 mm to 6.0 mm, as shown in Table 1, where U-1 to U-5 are the upper splint offsets (shown in parentheses) and L-A to L-D are the lower splint offsets (shown in parentheses).

TABLE 1

|  | U-1 (0.0 mm) | U-2 (1.0 mm) | U-3 (2.0 mm) | U-4 (3.0 mm) | U-5 (4.0 mm) |
| --- | --- | --- | --- | --- | --- |
| L-A (0.0 mm) | 0.0 mm | 1.0 mm | 2.0 mm | 3.0 mm | 4.0 mm |
| L-B (0.5 mm) | 0.5 mm | 1.5 mm | 2.5 mm | 3.5 mm | 4.5 mm |
| L-C (1.0 mm) | 1.0 mm | 2.0 mm | 3.0 mm | 4.0 mm | 5.0 mm |
| L-D (2.0 mm) | 2.0 mm | 3.0 mm | 4.0 mm | 5.0 mm | 6.0 mm |

Thus, twenty different mandibular advancements can be obtained with only nine different splints, four lower splints and five upper splints.

Depending on the clinician's prescription need, the clinician chooses any reasonable value for the offset of the upper fin relative to the lower fin, and as many offsets as the clinician desires. Since the digital manufacturing process accurately and precisely reproduces the splints, the combination of splints is repeatable, regardless of when the clinician orders several splints or splints with other offset distances.

Another advantage of the disclosed splint combination is enabling the creation of the same offset with different combinations of upper and lower splint positions. For example, as shown in Table 1, a 3.0 mm offset may be created using three different combinations of upper and lower fins (L-A/U-4, L-C/U-3, and L-D/U-2). Varying the combined position of the two fins allow better alignment of the fins within the mouth for reasons of patient comfort and clinical requirements.

Figure 9:
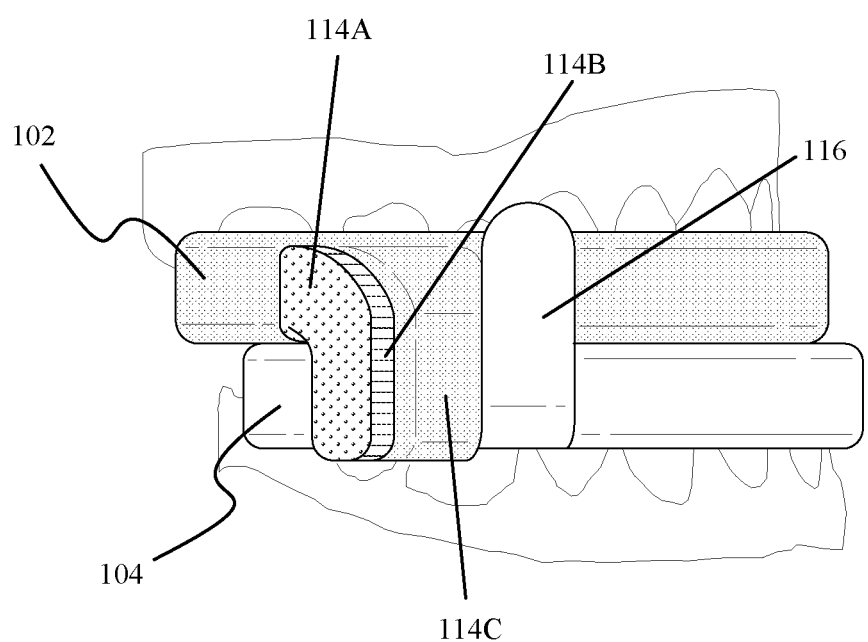
FIG. 9 shows three upper splints superimposed on each other for illustration purposes.

FIG. 9 illustrates the titration. Three separate upper splints 102 are provided, one having an upper fin offset of 1 mm (114-A), one having an upper fin offset of 2 mm (114-B), and one having an upper fin offset of 3 mm (114-B) (FIG. 9 shows all three of these upper splints superimposed on each other for illustration purposes. In actuality, they are separate splints.) One lower splint 104, having a lower fin offset of 0.5 mm (116) is also provided. Not shown is a lower splint 104 having a lower fin offset of 0 mm. The following combinations of splints provide the mandibular advancements of Table 2.

TABLE 2

|  | Upper | | |
| --- | --- | --- | --- |
| Lower | 1.0 mm | 2.0 mm | 3.0 mm |
| 0.0 mm | 1.0 mm | 2.0 mm | 3.0 mm |
| 0.5 mm | 1.5 mm | 2.5 mm | 3.5 mm |

In another aspect, disclosed herein are methods of reducing partial constriction of airway during sleep for a patient, the method comprising identifying a patient in need thereof; and administering to the patient the mandibular advancement device as disclosed herein.

In another aspect, disclosed herein are methods of manufacturing a mandibular advancement device, the method comprising obtaining measurements from a patient's dentition; digitally designing a mandibular advancement device; and milling the mandibular advancement device. In some embodiments, the obtaining measurement step comprises obtaining a dental impression.

What is claimed is:

1. A method of manufacturing a set of at least two mandibular advancement devices, the method comprising the steps of:
    obtaining electronic data on the shape of an individual's dentition;
    digitally designing a set of at least two mandibular advancement devices according to the obtained data;
    wherein the set of at least two mandibular advancement devices comprise:
        a first mandibular advancement device and a second mandibular advancement device,
            the first mandibular advancement device comprising a first upper splint and a first lower splint;
            the first upper splint comprises one or more upper fins, wherein each upper fin is located at a first distance UD from back of the first upper splint;
            the first lower splint comprises one or more lower fins, wherein each lower fin is located at a first distance LD from back of the first lower splint;
        the second mandibular advancement device comprising a second upper splint and a second lower splint;
            the second upper splint comprises one or more upper fins, wherein each upper fin is located at a second distance UD from back of the second upper splint;
            the second lower splint comprises one or more lower fins, wherein each lower fin is located at a second distance LD from back of the second lower splint;

each upper and lower splint is independently arch-shaped;

each upper and lower splint independently comprises an imprint of the patient's dentition along a plane of the splint contacting the dentition;

each fin is "L" shaped, with the leg of the "L" connecting the fin to its respective splint protruding along the occlusal plane buccally, while the other leg of the "L" protruding perpendicular to the occlusal plane away from the patient's gingiva;

each splint and its respective fins comprise a single contiguous unit;

automatedly milling each of the splints from a single polymeric block according to the digital design;

wherein each distance UD and each distance LD is unchangeable;

wherein:
i) the first distance UD is different than the second distance UD;
ii) the first distance LD is different than the second distance LD; or
iii) both the first distance UD is different than the second distance UD and the first distance LD is different than the second distance LD;

wherein the sum of the first distance UD and the first distance LD is different than the sum of the second distance UD and the second distance LD by an increment of 0.5 mm in the range of 0.5 mm to 6.0 mm;

wherein each upper fin comprises a front surface and each lower fin comprises a back surface, wherein when the upper and lower splints are worn by the individual, the front surface of the upper fin contacts the back surface of the lower fin along a contact surface; and wherein when the patient's mouth is opened during sleep, the contact between the front surface of the upper fin and the back surface of the lower fin is maintained.

2. The method of claim 1, further comprising using a computer aided design (CAD) process for the digital design.

3. The method of claim 1, wherein each of the first and second upper splint and lower splint independently comprises an empty center, wherein the empty center provides room for a patient's tongue when the device is in use.

4. The method of claim 1, wherein a rake angle of the contact surface is selected from the group consisting of a neutral angle, a recline angle, and a procline angle.

5. The method of claim 1, wherein the shape of each upper fin and each lower fin is independently selected from a predesigned digital library of fins.

6. The method of claim 1, further comprising including a gap between the lower fin and the lower splint in the digital design.

7. The method of claim 1, further comprising a gap between the upper fin and the upper splint in the digital design.

8. The method of claim 1, further comprising in the digital design two or more gaps between the lower fin and each of the first and second lower splint, or further comprising two or more gaps between the upper fin and the first and second upper splint, wherein the gaps are between the patient's dentition and each of the lower splint or upper splint, and wherein the gaps are digitally designed to be varied in size, wherein the varied-sized gaps optimize the retention of the device on the patient's dentition.

9. The method of claim 1, wherein one of the first or second upper splint is designed to contact one of the first or second lower splint along a plane, wherein the plane is the same as a patient's occlusal plane.

10. The method of claim 1, wherein one of the first or second lower splint is designed to contact one of the first or second upper splint along a plane, wherein the plane is the same as a patient's occlusal plane.

11. The method of claim 1, further comprising in the digital design one or more structural feature configured to accommodate an add on selected from the group consisting of a support member, a ball clasp, retention wire, treatment wire, alignment wires, and a tongue behavior modification wire.

12. The method of claim 1, further comprising one or more retention arms in the digital design.

* * * * *